(12) United States Patent
Hu et al.

(10) Patent No.: US 8,634,677 B2
(45) Date of Patent: Jan. 21, 2014

(54) PACS OPTIMIZATION TECHNIQUES

(75) Inventors: Xiao Hu, Los Angeles, CA (US); Robert C. Platt, III, Encino, CA (US); Vesselin Zlatev, Aliso Viejo, CA (US); Farzad D. Buxey, Marina Del Ray, CA (US)

(73) Assignees: The Regents of the University of California, Oakland, CA (US); Global Care Quest, Inc., Aliso Viejo, CA (US)

( * ) Notice: Subject to any disclaimer, the term of this patent is extended or adjusted under 35 U.S.C. 154(b) by 1072 days.

(21) Appl. No.: 12/413,946

(22) Filed: Mar. 30, 2009

(65) Prior Publication Data

US 2010/0246981 A1    Sep. 30, 2010

(51) Int. Cl.
*G06K 9/54* (2006.01)
*G06K 9/60* (2006.01)

(52) U.S. Cl.
USPC ........................................ 382/305

(58) Field of Classification Search
USPC ......... 382/128, 232, 233, 240, 248, 298, 305; 705/2; 709/203
See application file for complete search history.

(56) References Cited

U.S. PATENT DOCUMENTS

| | | |
|---|---|---|
| 5,553,609 A | 9/1996 | Chen et al. |
| 5,713,350 A | 2/1998 | Yokota et al. |
| 5,823,948 A | 10/1998 | Ross, Jr. et al. |
| 5,827,180 A | 10/1998 | Goodman |
| 5,832,488 A | 11/1998 | Eberhardt |
| 5,867,821 A | 2/1999 | Ballantyne et al. |
| 5,924,074 A | 7/1999 | Evans |
| 5,950,207 A | 9/1999 | Mortimore et al. |
| 5,960,403 A | 9/1999 | Brown |
| 6,049,794 A | 4/2000 | Jacobs et al. |
| 6,182,029 B1 | 1/2001 | Friedman |
| 6,226,620 B1 | 5/2001 | Oon |
| 6,246,992 B1 | 6/2001 | Brown |

(Continued)

FOREIGN PATENT DOCUMENTS

| | | |
|---|---|---|
| EP | 1217556 A2 | 6/2002 |
| JP | 10027165 A | 1/1998 |

(Continued)

OTHER PUBLICATIONS

Wayne T. DeJarnette, "Web technology and its relevance to PACS and teleradiology", Applied Radiology, pp. 9-12, Aug. 2000.*

(Continued)

*Primary Examiner* — Phuoc Tran
(74) *Attorney, Agent, or Firm* — St. Onge Steward Johnston & Reens LLC

(57) ABSTRACT

Some embodiments provide a method and system for efficiently transferring medical images. Some embodiments receive a medical image in a first platform dependent format of a Picture Archiving and Communication System (PACS). The first platform dependent format is one that is accessible by a first format compliant device that includes a library that specifies how to decode the first format. Some embodiments transform the medical image from the first format to a second format. The second format includes decoded content of the first format that is viewable on a first format non-compliant device. The transformed image is then passed to the device for viewing. Additionally, some embodiments efficiently transfer medical images by identifying image settings for one or more devices and by passing requested images that are optimized by resizing the images according to the image settings of the requesting device.

21 Claims, 15 Drawing Sheets

(56) References Cited

U.S. PATENT DOCUMENTS

| | | | |
|---|---|---|---|
| 6,283,761 B1 | 9/2001 | Joao | |
| 6,375,614 B1 | 4/2002 | Braun et al. | |
| 6,523,009 B1 | 2/2003 | Wilkins | |
| 6,611,846 B1 | 8/2003 | Stoodley | |
| 6,711,297 B1 * | 3/2004 | Chang et al. | 382/240 |
| 6,925,208 B1 * | 8/2005 | Huffman | 382/232 |
| 7,165,221 B2 | 1/2007 | Monteleone et al. | |
| 7,379,605 B1 * | 5/2008 | Ticsa | 382/232 |
| 7,424,679 B1 | 9/2008 | Lamer et al. | |
| 7,853,241 B1 * | 12/2010 | Harrison | 455/406 |
| 7,979,387 B2 * | 7/2011 | Wright et al. | 707/609 |
| 2002/0194029 A1 | 12/2002 | Guan et al. | |
| 2003/0140044 A1 | 7/2003 | Mok et al. | |
| 2004/0073453 A1 | 4/2004 | Nenov et al. | |
| 2004/0186746 A1 | 9/2004 | Angst et al. | |
| 2006/0064328 A1 | 3/2006 | Datta et al. | |
| 2007/0005397 A1 | 1/2007 | Lee | |
| 2007/0118540 A1 | 5/2007 | Guo | |
| 2008/0021741 A1 * | 1/2008 | Holla et al. | 705/3 |
| 2008/0052115 A1 * | 2/2008 | Spradley et al. | 705/2 |

FOREIGN PATENT DOCUMENTS

| | | |
|---|---|---|
| JP | 11239165 A | 8/1999 |
| JP | 2001345961 A | 12/2001 |
| JP | 2002041550 A | 2/2002 |
| JP | 2002132642 A | 5/2002 |
| JP | 2003091595 A | 3/2003 |
| JP | 2003324737 A | 11/2003 |
| JP | 2004344390 A | 12/2004 |
| JP | 2005293029 A | 10/2005 |
| JP | 2006141500 A | 6/2006 |
| JP | 2006141508 A | 6/2006 |
| JP | 2006260232 A | 9/2006 |
| JP | 2007148660 A | 6/2007 |
| JP | 2007323378 A | 12/2007 |
| JP | 2008293264 A | 12/2008 |
| WO | 02077863 A2 | 10/2002 |
| WO | 2008011063 A2 | 1/2008 |
| WO | 2008077232 A1 | 7/2008 |
| WO | 2008084330 A2 | 7/2008 |

OTHER PUBLICATIONS

Donglan Yu, et al.; "A XML-Based Remote EMI Sharing System Conformable to Dicom"; IEEE May 30, 2008; pp. 556-559.

You, et al.; "Application of XML in DICOM"; Medical Imaging 2005 (SPIE) pp. 446-454.

European Search Report; Application No. EP 10 15 8471; Issued: Jul. 6, 2012; Mailing Date Jul. 16, 2012; 8 pages.

Robert C. Leif; "A DICOM Compatible Format for Analytical Cytology Data, that can be Expressed in XML"; Proceedings of SPIE, America, SPIE, Jan. 24, 2001, vol. 4260, pp. 238-248.

European Search Report, Application No. EP 10158471.2-1951/2237179, Mailing Date: Feb. 25, 2013; Mailing Date: Mar. 5, 2013, 14 pages.

* cited by examiner

```
function FetchDicomStudy(szPatID, szStudyID)                        410
{
        var DQO      = new ActiveXObject("DicomQueryObject.DicomQuery.1");
        var rtnXMLDoc = new ActiveXObject("Microsoft.XMLDOM");  ———— 420

DQO.szAETitle       = ScriptHelper.Config("DQO AE Title");
        DQO.szRemoteAETitle = ScriptHelper.Config("DQO Remote AE Title");
        DQO.szListenerAETitle = ScriptHelper.Config("DQO Listener AE Title");

try {
                var rs = new ActiveXObject("ADODB.Recordset");
                rs.Open("select fetchlog from dicomstudy where studyid='"+ szStudyID + "'",
Connection, adOpenStatic,adLockOptimistic);
        }
        try {
                responseXml = DQO.RequestAStudy(szPatID,szStudyID);
                if (DQO.GetLastError() >= 0 && responseXml.length > 0)
                {
                        if (!rs.EOF)
                        { rs("fetchlog").AppendChunk("DQO returned with:" + responseXml); } rtnXMLDoc.loadXML(responseXml);
                        var aNodeList = rtnXMLDoc.documentElement.selectNodes("//xml/move");
                        var aNode = aNodeList.nextNode;
                        var nFail = 1;

if (aNode != null)
                        {
                                nFail   = Number(aNode.selectSingleNode("@failed").value);
                        }
                        if (!rs.EOF)
                        {
                           rs.Update();
                           rs.Close();
                        }
                        if (nFail == 0)
                                return 1;
                }
                return -1; } }
```

*Figure 4*

```
function GetDicomStudyList(szPatID) {
        var DQO = new ActiveXObject("DicomQueryObject.DicomQuery.1");     510
        var rtnXMLDoc = new ActiveXObject("Microsoft.XMLDOM"); var szXML;  520
        DQO.szAETitle = ScriptHelper.Config("DQO AE Title");
        DQO.szRemoteAETitle = ScriptHelper.Config("DQO Remote AE Title");

try { szXML = DQO.GetListOfStudies(szPatID, null, null); }
        if (DQO.GetLastError() >= 0 && szXML.length > 0)
        {       try { rtnXMLDoc.loadXML(szXML); }
                try {
                        var rs = new ActiveXObject("ADODB.Recordset");
                        var aCommand = new ActiveXObject("ADODB.Command");
                        var aParam =  new ActiveXObject("ADODB.Parameter");
                        aCommand.ActiveConnection = Connection;
                        aCommand.CommandType = 4;
                        aCommand.CommandText = "q_AddDicomStudy";
                        aParam =
aCommand.CreateParameter("szPatID",adVarChar,adParamInput,20,PatRef.PatId);
                        aCommand.Parameters.Append(aParam);
                        aParam =
aCommand.CreateParameter("szStudyId",adVarChar,adParamInput,128,"");
                        aCommand.Parameters.Append(aParam);
                        aParam =
aCommand.CreateParameter("StudyDateTime",adDate,adParamInput,4,"12/01/2002 0:0" );
                        aCommand.Parameters.Append(aParam);
                        aParam =
aCommand.CreateParameter("szModality",adVarChar,adParamInput,16,"UK");
                        aCommand.Parameters.Append(aParam);
                        aParam =
aCommand.CreateParameter("szDescription",adVarChar,adParamInput,128,"");
                        aCommand.Parameters.Append(aParam);
                        aParam =
aCommand.CreateParameter("szAccession",adVarChar,adParamInput,50,"");
                        aCommand.Parameters.Append(aParam); }
                try {
                        var aNodeList = rtnXMLDoc.documentElement.selectNodes("//xml/study");
                        var aNode = aNodeList.nextNode;  var nEntered = 0;
                        while(aNode != null) {
                                aCommand.Parameters("szPatID") = szPatID;
                                aCommand.Parameters("szStudyId")    =
aNode.selectSingleNode("@studyUID").value;
                                aCommand.Parameters("StudyDateTime") =
aNode.selectSingleNode("@date").value;
                                aCommand.Parameters("szModality")    =
aNode.selectSingleNode("@modality").value;
                                aCommand.Parameters("szDescription")  =
aNode.selectSingleNode("@description").value;
                                aCommand.Parameters("szAccession")  =
aNode.selectSingleNode("@accession").value;
                                aCommand.Execute(); nEntered = nEntered + 1;
                                aNode = aNodeList.nextNode;} return nEntered;}}}
```

*Figure 5*

```
1005
   ↓
        <all version="2">
            <attr id="0008_0000" desc="Group 0008 Length" vr="UL" vm="1">
                <val id="1" value="40"/>
1045        </attr>
   ↘    <attr id="0008_0008" desc="Image Type" vr="CS" vm="3">
            <val id="1" value="ORIGINAL"/>
            <val id="2" value="PRIMARY"/>
            <val id="3" value="OTHER"/>
        </attr>
            <attr id="0008_0016" desc="SOP Class UID" vr="UI" vm="1">
                <val id="1" value="1.2.840.10008.5.1.4.1.1.4"/>      1030
            </attr>
        <attr id="0008_0020" desc="Study Date" vr="DA" vm="1">
            <val id="1" value="20050525"/>
        </attr>
            <attr id="0008_0030" desc="Study Time" vr="TM" vm="1">
                <val id="1" value="093837"/>
            </attr>
            <attr id="0008_0050" desc="Accession Number" vr="SH" vm="1">
                <val id="1" value="2446935"/>
            </attr>
            <attr id="0008_0060" desc="Modality" vr="CS" vm="1">
                <val id="1" value="MR"/>                              1010
            </attr>
        <attr id="0008_1030" desc="Study Description" vr="LO" vm="1">
            <val id="1" value="MRI BRAIN W&WO/CON_CLO"/>
        </attr>
            <attr id="0008_103E" desc="Series Description" vr="LO" vm="1">
                <val id="1" value="         "/>
            </attr>
            <attr id="0008_1110" desc="Ref Study Seq" vr="SQ" vm="1">
                <attr id="0008_0000" desc="Group 0008 Length" vr="UL" vm="1">
                    <val id="1" value="88"/>
                </attr>
                <attr id="0008_1150" desc="Ref SOP Class UID" vr="UI" vm="1">
                    <val id="1" value="1.2.840.10008.3.1.2.3.1"/>
                </attr>
                <attr id="0008_1155" desc="Ref SOP Inst UID" vr="UI" vm="1">
                    <val id="1" value="1.2.840.113745.101000.1008000"/>
                </attr>
            </attr>
            <attr id="0010_0000" desc="Group 0010 Length" vr="UL" vm="1">
                <val id="1" value="100"/>                             1020
            </attr>
        <attr id="0010_0010" desc="Patient's Name" vr="PN" vm="1">
            <val id="1" value="Richardson^Rich"/>
        </attr>
            <attr id="0010_0020" desc="Patient ID" vr="LO" vm="1">
                <val id="1" value="D000002"/>
            </attr>
            <attr id="0010_0030" desc="Patient's Birth Date" vr="DA" vm="1">
                <val id="1" value="19500101"/>
            </attr>
            <attr id="0010_0040" desc="Patient's Sex" vr="CS" vm="1">
                <val id="1" value="M"/>
            </attr>
            <attr id="0010_1010" desc="Patient's Age" vr="AS" vm="1">
                <val id="1" value="000Y"/>
            </attr>
        </all>
```

Function GenXml ( xml, root_node )          1110
        Loop until root_node.is_end
                tag = root_node.next_tag
                vr = tag.value_representation
                vm = tag.value_multiplicity xnode = add node ( "attr" ) to xml
                add attributes to xnode:
                        add ( "id", tag.id )
                        add ( "desc", tag.description )
                        add ( "vr", vr )
                        add ( "vm", vm )

1120
                switch on vr
                        case SQ // Sequence
                                Loop count = 0 to vm
                                        Call GenXml ( xnode, tag.value[count] )
                                End Loop case AE, SS, etc: // Strings
                                Loop count = 0 to vm
                                        val = add node ( "val" ) to xnode
                                        add attributes to val:
                                                add ( "id", count )
                                                add ( "value", tag.value[count] )

End Loop

*Figure 11*

PACS OPTIMIZATION TECHNIQUES

FIELD OF THE INVENTION

The invention relates to the field of health care. More specifically, to methods and systems for efficiently transferring medical images from an image store to one or more devices.

BACKGROUND OF THE INVENTION

The quality of health care is constantly evolving and improving. These improvements often include better medical techniques and medical practices, but may also include improvements to patient data management. By better acquiring, managing, and disseminating patient data, health care providers are able to free themselves from mundane data entry and data acquisition tasks. These tasks can consume time that could be otherwise allocated to providing care.

Many hospitals now acquire and store patient data digitally. By storing patient data digitally, health care providers have the ability to quickly search and access patient data from anywhere in the hospital at any time. However, transitioning to digital patient data posed several data compatibility issues. Data that was entered using a first format or device may not necessarily have been compatible with data that was entered using a second format or device. This was often the case as different manufacturers created different imaging devices for specialized purposes within the hospital, each device having different interfaces and different file formats that were often proprietary. As a result, standards were established to ensure interoperability of the digital data.

The Digital Imaging and Communications in Medicine (DICOM) is one such established standard for digital medical imaging. A DICOM compatible device or application is guaranteed to be able to generate, produce, display, send, query, store, process, retrieve, or print any DICOM compatible image. DICOM is now used for imaging in radiology, cardiology, oncology, dentistry, surgery, neurology, mammography, radiotherapy, opthalmology, orthopedics, pediatrics, pathology, veterinary, etc. As such, DICOM is currently the preferred standard for implementing a Picture Archiving and Communication Systems (PACS) that provides a central image store for storing, retrieving, distributing, and presenting images in a hospital or other health care environment. This further ensures that by purchasing a DICOM compliant device, the hospital will be able to seamlessly integrate such a device into a Hospital Information System (HIS) and have the device view and access any image within the PACS.

The DICOM standard specifies a particular file format definition that must be adhered to in order to ensure the intercompatability and interoperability of the various devices within the HIS. Additionally, DICOM specifies a network communications protocol for the transmission and dissemination of these medical images. Therefore, a device that is compatible with the DICOM standard is a specialized device. Such a compatible device necessarily includes one or more libraries to parse and process the file format or to communicate (e.g., send and receive) using the communications protocol.

By requiring these libraries and protocols, the DICOM standard excludes many devices that are commonly used within the health care environment from being able to access digital medical images. For example, many smartphones, cellular telephones, or Personal Digital Assistants (PDAs) that are able to wirelessly communicate and display low resolution or high resolution images are unable to process DICOM formatted images. In some instances, these devices may be made compatible by including the necessary DICOM functionality (e.g., libraries), but at the expense of increased memory, processing, and ultimately cost that could render such functionality useless. Instead, the hospital has to invest in specialized hardware and proprietary software to fully realize the benefits that may be gleaned from a PACS that operates using the DICOM standard.

Therefore, there is a need in the art to maintain the interoperability provided by DICOM while reducing the overhead associated with adhering to the DICOM standard. For example, there is a need to enable more conventional devices (e.g., smartphones, cellular telephones, PDAs, etc.) to be utilized as compatible PACS viewing platforms irrespective of their lack of DICOM functionality. In other words, there is a need to enable these devices to send, receive, and view DICOM formatted images without necessitating change in these devices, thereby reducing costs of the health care provider.

SUMMARY OF THE INVENTION

Some embodiments provide a method and system for efficiently transferring medical images from an image database, such as a Picture Archiving and Communication Systems (PACS), to one or more different display devices. Some embodiments perform the efficient transfer of the images by optimizing the images before transferring the images to a client device based on specifications of the client device. Some embodiments optimize the images by preprocessing the images as the images are stored to the PACS. Some embodiments optimize the images on-demand as the images are requested by and sent to the client device.

Some embodiments optimize the images by converting platform dependent image files that are viewable only on specialized or proprietary devices to platform independent images files that are viewable by any standard image viewing application of one or more different client devices. In some such embodiments, the PACS stores the medical images in the platform dependent format. The platform dependent format requires the client devices to have specialized libraries in order to decode and process the images. These specialized libraries must reside on the client device. Additionally, these libraries require additional computation to occur at the client device in order for the client device to decode the format and produce a viewable image.

Some embodiments optimize the images stored in the PACS for display on multiple different receiving devices by modifying the platform dependent file format of the stored images to the platform independent file format before transferring the images to the devices for display. In this manner, some embodiments offload the processing requirements required for the proprietary decoding of the platform dependent file format from the client display device. Furthermore, the client display device can display the medical image without storing the corresponding library for performing the decoding functionality. Therefore, some embodiments also offload the memory requirements from the display device such that a display device with minimal processing or memory resources may be used to display the medical image. For instance, the display device may include a pocket PC, smartphone, cellular telephones, or Personal Digital Assistants (PDAs) with some basic image rendering capabilities.

Some embodiments generate an Extensible Markup Language (XML) formatted header as the platform independent file format. The generated XML header is used in some embodiments to replace the platform dependent file format.

XML is one example of a platform independent file format that is executable on multiple different computing platforms (e.g., Microsoft Windows® and Apple Mac OS®) and for which several applications currently exist that do not require proprietary or licensed decoding libraries in order to decode and process the XML format. It should be apparent to one of ordinary skill in the art that some embodiments use any number of platform independent file formats in addition to or in place of the XML file format. The platform dependent file format may include any number of proprietary formats such as the Digital Imaging and Communications in Medicine (DICOM) format where DICOM is used to initially transfer and store the image within the PACS. Without the image optimization to the platform independent file format, the DICOM format requires specialized libraries on the display device to decode the DICOM format. In many instances, the use of these specialized libraries incurs licensing costs. Furthermore, since the libraries are platform specific, the libraries may be incompatible with software or hardware of many generally available client devices. For example, some smartphones today currently operate with the Microsoft Windows Mobile® operating system whereas other smartphones operate with the Palm® operating system or the Symbian® operating system, where each such operating system would require a different proprietary decoding library.

Additionally, some embodiments implement robust queries over the images of the PACS using the platform independent format. The platform independent format allows for greater flexibility as XML tags may be used separately or together to specify any number of customizable queries. This allows users the ability to search for images using queries that would otherwise be invalid under the platform dependent format.

Some embodiments perform the image optimization and efficient image transfer by resizing the image data according to image display settings of a client display device. Specifically, by down sampling the image to the image settings of the device, some embodiments reduce the image data of a medical image that is transferred to the display device without reducing quality of the medical image. For instance, an original image having a resolution of 1600×1200 is resized to a resolution of 320×240 before transfer to a display device having a corresponding resolution of 320×240. In this manner, the image is transferred quicker and with less latency from an image store to the display device. Some embodiments perform this optimization at preprocessing when an image is initially stored or updated to the PACS or on-demand upon user request for the image.

During preprocessing or on-demand processing, some embodiments generate a set of resized images for a set of different image settings. Each resized image has a reduced set of image data that does not compromise the image quality when displayed using a device with a corresponding display setting. By identifying image settings of the display device, some embodiments transfer only the resized image that corresponds to the identified display settings and thus avoid transferring unnecessary image data.

Some embodiments optimize the image transfer by compressing the image file to be transferred. This provides an additional means for reducing the amount of image data that is transferred to the display device. Some embodiments compress the resized image data, the modified header, the original image data, the original header, or some combination of the header and image data to achieve a more efficient transfer of the image.

It should be apparent to one of ordinary skill in the art that some embodiments optimize an image using one or more of the above described techniques separately or in combination with one another. As such, some embodiments achieve different levels of optimization depending on a desired level of optimization.

BRIEF DESCRIPTION OF THE DRAWINGS

The novel features of the invention are set forth in the appended claims. However, for purpose of explanation, several embodiments of the invention are set forth in the following figures.

FIGS. 4 and 5 present exemplary functions of a script that is processed by the MedServer to retrieve a client requested image from the image optimization module in accordance with some embodiments.

FIG. 10 illustrates contents of a DICOM formatted header that has been converted to an XML formatted header in accordance with some embodiments of the invention.

FIG. 11 illustrates pseudo-code for converting a DICOM formatted header to a XML formatted header.

DETAILED DESCRIPTION OF THE INVENTION

Figure 1:
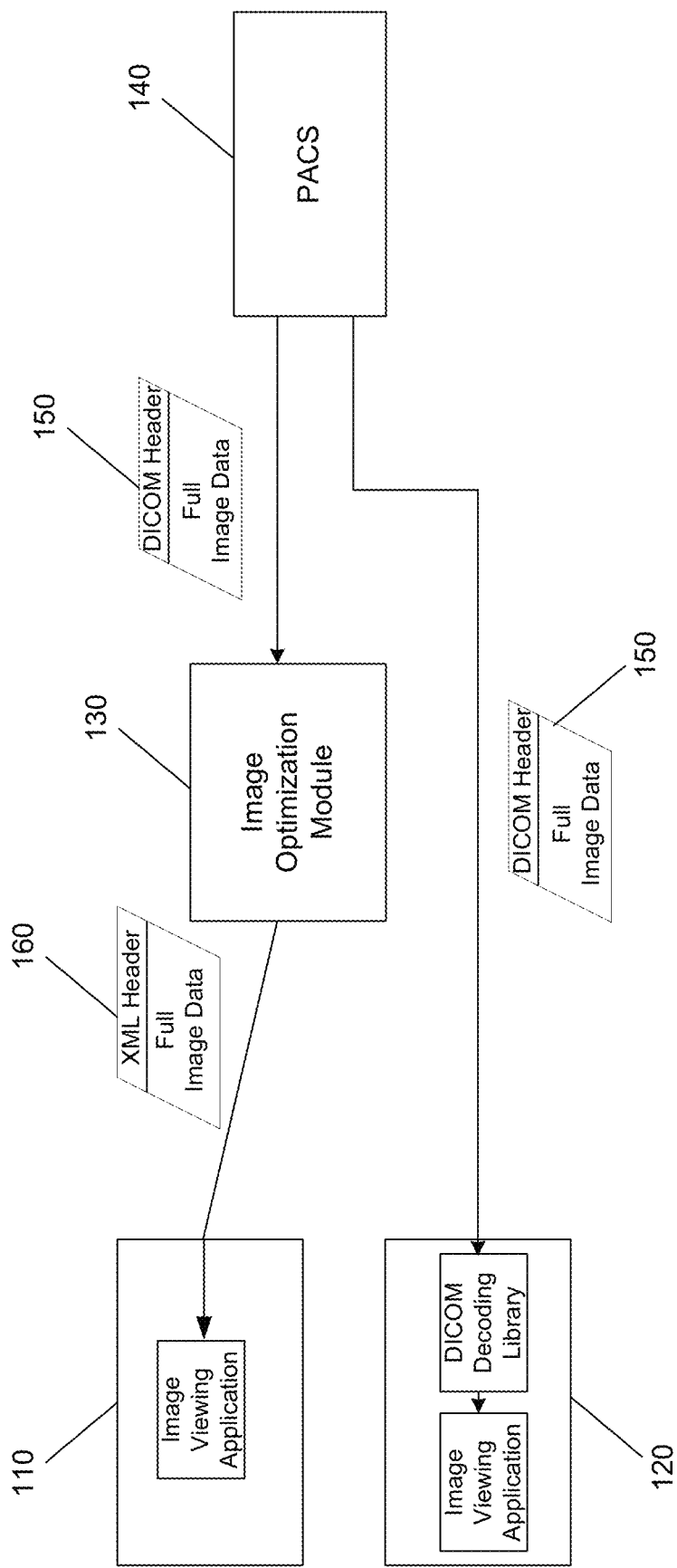
FIG. 1 conceptually illustrates converting a platform dependent file format of a medical image to a platform independent file format in accordance with some embodiments.

In the following detailed description of the invention, numerous details, examples, and embodiments of the invention are set forth and described. However, it will be clear and apparent to one skilled in the art that the invention is not limited to the embodiments set forth and that the invention may be practiced without some of the specific details and examples discussed.

I. Overview

Some embodiments provide a method and system for efficiently transferring medical images from an image database, such as a Picture Archiving and Communication Systems (PACS), to one or more different display devices. Some embodiments perform the efficient transfer of the images by optimizing the images before transferring the images to a client device based on specifications of the client device.

Some embodiments optimize the images by preprocessing the images as the images are stored to the PACS. Some embodiments optimize the images on-demand as the images are requested by and sent to the client device.

Some embodiments optimize the images by converting platform dependent image files that are viewable only on specialized or proprietary devices to platform independent images files that are viewable by any standard image viewing application of one or more different client devices. In some such embodiments, the PACS stores the medical images in the platform dependent format. The platform dependent format requires the client devices to have specialized libraries in order to decode and process the images. These specialized libraries must reside on the client device. Additionally, these libraries require additional computation to occur at the client device in order for the client device to decode the format and produce a viewable image.

Some embodiments optimize the images stored in the PACS for display on multiple different receiving devices by modifying the platform dependent file format of the stored images to the platform independent file format before transferring the images to the devices for display. In this manner, some embodiments offload the processing requirements required for the proprietary decoding of the platform dependent file format from the client display device. Furthermore, the client display device can display the medical image without storing the corresponding library for performing the decoding functionality. Therefore, some embodiments also offload the memory requirements from the display device such that a display device with minimal processing or memory resources may be used to display the medical image. For instance, the display device may include a pocket PC, smartphone, cellular telephones, or Personal Digital Assistants (PDAs) with some basic image rendering capabilities.

Some embodiments generate an Extensible Markup Language (XML) formatted header as the platform independent file format. The generated XML header is used in some embodiments to replace the platform dependent file format. XML is one example of a platform independent file format that is executable on multiple different computing platforms (e.g., Microsoft Windows® and Apple Mac OS®) and for which several applications currently exist that do not require proprietary or licensed decoding libraries in order to decode and process the XML format. It should be apparent to one of ordinary skill in the art that some embodiments use any number of platform independent file formats in addition to or in place of the XML file format. The platform dependent file format may include any number of proprietary formats such as the Digital Imaging and Communications in Medicine (DICOM) format where DICOM is used to initially transfer and store the image within the PACS. Without the image optimization to the platform independent file format, the DICOM format requires specialized libraries on the display device to decode the DICOM format.

Additionally, some embodiments implement robust queries over the images of the PACS using the platform independent format. The platform independent format allows for greater flexibility as XML tags may be used separately or together to specify any number of customizable queries. In many instances, the use of these specialized libraries incurs licensing costs. Furthermore, since the libraries are platform specific, the libraries may be incompatible with software or hardware of many generally available client devices. For example, some smartphones today currently operate with the Microsoft Windows Mobile® operating system whereas other smartphones operate with the Palm® operating system or the Symbian® operating system, where each such operating system would require a different proprietary decoding library.

FIG. 1 conceptually illustrates converting a platform dependent file format of a medical image to a platform independent file format in accordance with some embodiments. This figure includes a DICOM compliant client 120, a DICOM non-compliant client 110, an image optimization module 130 of some embodiments, and a PACS 140.

In this figure, the PACS 140 stores medical images using the DICOM file format. Accordingly, each image includes a DICOM formatted header 150. Only DICOM compliant clients, such as client 120, are able to directly access, decode, and view a medical image from the PACS 140. The DICOM compliant client 120 internally stores the necessary DICOM libraries that enable the device to recognize and decode the DICOM file format. The client 120 therefore allocates a portion of its memory resources to store the one or more DICOM libraries. In many instances, the decoding associated with such a proprietary format has greater computational overhead than decoding of platform independent file format.

By utilizing the image optimization module 130 of some embodiments, many devices commonly used by health care professionals that are not DICOM compliant can nevertheless be enabled to access and view the DICOM formatted image files. As shown, the image optimization module 130 of some embodiments converts the DICOM formatted header 150 to an XML formatted header 160 before the image is transferred to the DICOM non-compliant client 110. Since XML is a platform independent format, the client 110 may use any conventional image viewing application to parse and view the image data passed along with the XML header 160 that describes the image content. For instance, the client 110 may use an XML capable web browser with image rendering functionality as the image viewing application.

Conversely, the client 120 directly accesses the image 150 from PACS 140. As such, the image that the client 120 receives from the PACS 140 contains the DICOM formatted header. Therefore, in order to view the image data, the client 120 first decodes the proprietary DICOM header using a DICOM library. The DICOM library is stored locally on the client 120. The DICOM library allows the client to recognize and process the DICOM format. However, such processing requires additional computational resources of the client 120 that could otherwise have been performed by the image optimization module 130 of some embodiments. Furthermore, the DICOM library is often a proprietary library that requires the user of client 120 to pay licensing fees for the right to use the DICOM library.

Some embodiments perform the image optimization and efficient image transfer by resizing the image data according to image display settings of a client display device. Specifically, by down sampling the image to the image settings of the device, some embodiments reduce the image data of a medical image that is transferred to the display device without reducing quality of the medical image. In this manner, the image is transferred quicker and with less latency from an image store to the display device. Some embodiments perform this optimization at preprocessing when an image is initially stored or updated to the PACS or on-demand upon user request for the image.

During preprocessing or on-demand processing, some embodiments generate a set of resized images for a set of different image settings. Each resized image has a reduced set of image data that does not compromise the image quality when displayed using a device with a corresponding display setting. By identifying image settings of the display device, some embodiments transfer only the resized image that corresponds to the identified display settings and thus avoid transferring unnecessary image data.

Figure 2:
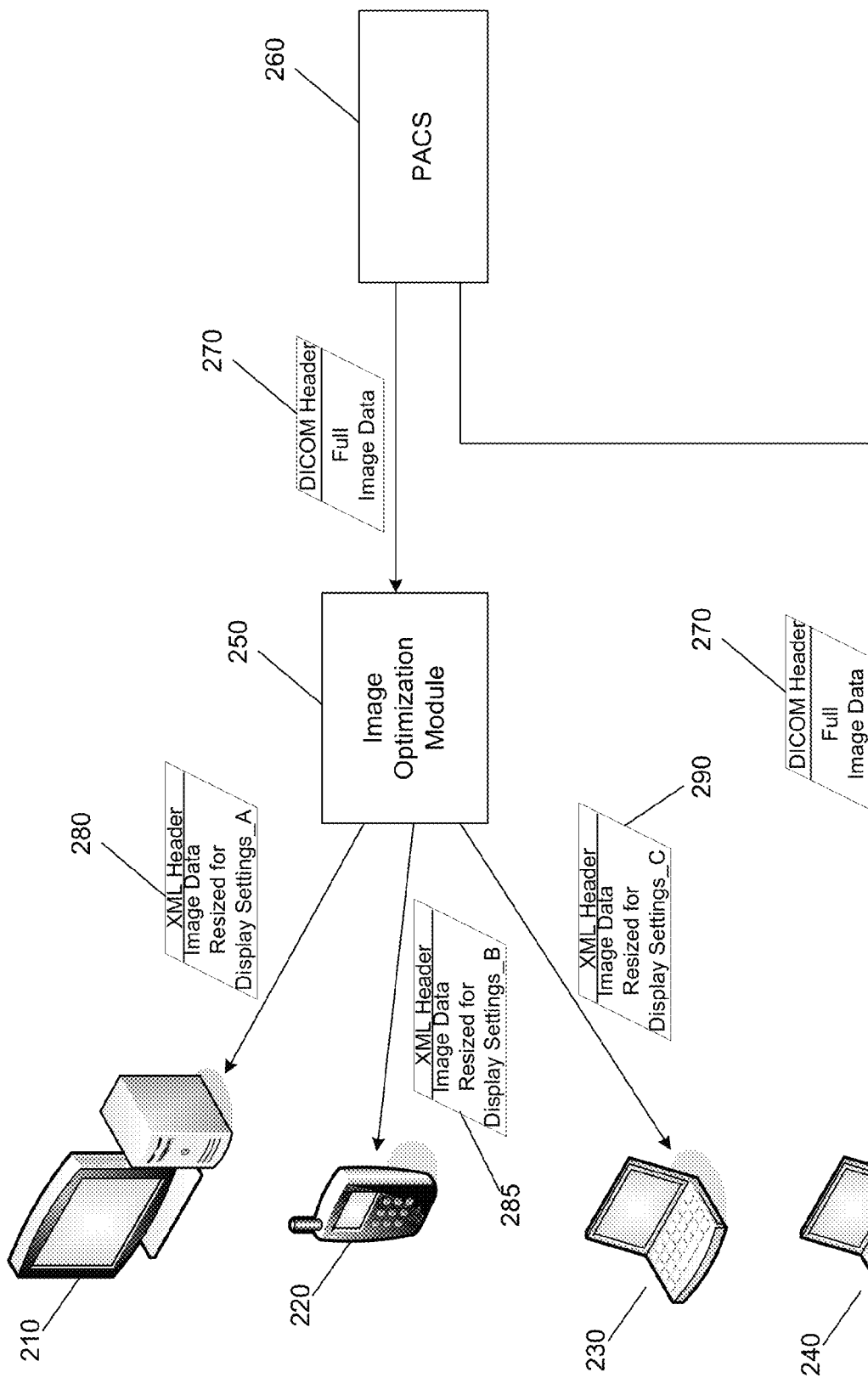
FIG. 2 illustrates the resizing of images performed by an image optimization module 250 of some embodiments.

FIG. 2 illustrates the resizing of images performed by an image optimization module 250 of some embodiments. The figure includes several client display devices 210-240, the image optimization module 250 of some embodiments, and a PACS 260. The PACS 260 stores an original image 270 that is requested by the client devices 210-240.

The image optimization module 250 generates multiple different resized images 280-290 from the original image 270. Each of the resized images is optimized for display on a particular client device based on image display settings of the client device. In some embodiments, the image optimization module 250 generates the resized images during preprocessing when the images are initially sent to the PACS 260 for storage. In some embodiments, the image optimization module 250 generates the resized images on-demand as each device 210-230 requests the image from the PACS 260.

In this figure, the client devices 210-240 have different image display settings. For instance, client 210 is a desktop computer with a large desktop display monitor. The client 210 will have a higher display resolution than the screen of a laptop computing device 230 and an even higher display resolution than a PDA or Smartphone device 220. Therefore, assuming the original image 270 has a display resolution of 2560×1980 pixels and the display of the computer 210 has a display resolution of 1280×960 pixels, the image optimization module 250 optimizes the image 270 for display on the client 210. Specifically, the image optimization module 250 down samples the image 270 to the 1280×960 display resolution of the device 210 such that the extraneous pixel information is not passed to the client 210. As shown in the figure, the image optimization module 250 passes the optimized image 280 instead of the original image 270 to the client device 210, where the optimized image 280 contains less pixel data than the original image 270.

Similarly, assuming the PDA 220 has a display resolution of 176×144 pixels, a large amount of the 2560×1980 pixel data is removed by the image optimization module 250 of some embodiments without loss of image quality when displaying the image on the client 220. In this instance, the resized image 285 passing from the image optimization module 250 to the device 220 is down sampled to have a display resolution of only 176×144. By removing this extraneous pixel data, some embodiments reduce the time for transferring an image from the PACS 260 to the client and reduce the processing performed on the client as only the necessary amount of data is passed. It should be apparent to one of ordinary skill in the art that the image optimization module 250 of some embodiments includes additional pixel data in the optimized image. The additional pixel data allows users to zoom into an image to view specific regions with more detail. However, such additional pixel data is less than the amount of pixel data of the original image, therefore resulting in an optimized image that is more efficiently transferred to the client device than when transferring the original image.

FIG. 2 also demonstrates a client 240 that directly retrieves images from the PACS 260. These images are not optimized for the image settings of the client 240. As such, extraneous image data is transferred to the client 240. For example, if the original image 270 has a resolution of 2560×1980 pixels and the client device has only a 1280×960 pixels resolution, then the client 240 will be receiving twice as much data than is necessary (2560×1980 pixels of the original image instead of 1280×960 pixels for the reduced image). Moreover, the processing burden is then placed on the device 240 to properly resize the image so that it fits on the 1280×960 pixel display.

Some embodiments optimize the image transfer by compressing the image file to be transferred. This provides an additional means for reducing the amount of image data that is transferred to the display device. Some embodiments compress the resized image data, the modified header, the original image data, the original header, or some combination of the header and image data to achieve a more efficient transfer of the image.

It should be apparent to one of ordinary skill in the art that some embodiments optimize an image using one or more of the above described techniques separately or in combination with one another. As such, different levels of optimization may be achieved.

Several more detailed embodiments of the invention are described in the sections below. Specifically, Section II describes an environment in accordance with some embodiments for implementing the efficient image transfer methodology. Section III provides several examples for preprocessing and on-demand processing of an image header to facilitate the efficient transfer of the image. Section IV then provides several examples for preprocessing and on-demand processing of the image data to facilitate the efficient transfer of the image. Lastly, Section V provides a description of a computer system with which some embodiments of the invention are implemented.

II. System Architecture

The image optimization module of some embodiments that performs the various image optimization functionality for efficiently transferring images is integrated into an existing Hospital Information System (HIS) as a component of the HIS. In some embodiments, the image optimization module is seamlessly integrated into the HIS in a manner that requires little to no modification to existing components within the HIS. For instance, a PACS of the HIS continues operating as an image database as the image optimization module optimizes the images being stored and retrieved from the PACS.

Figure 3:
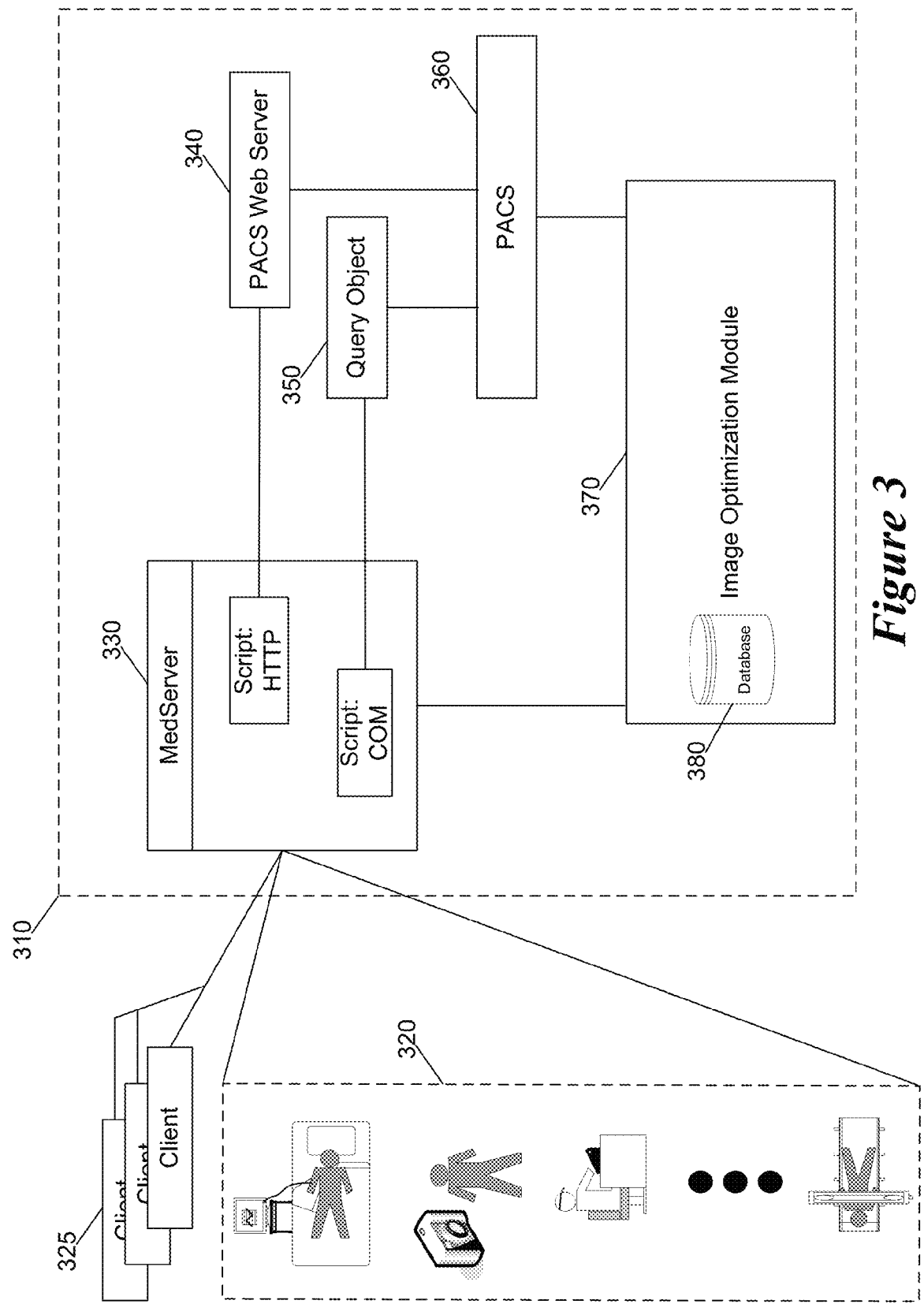
FIG. 3 illustrates an exemplary architecture of an HIS with an integrated image optimization module that preprocesses images as the images are stored within a PACS.

FIG. 3 illustrates an exemplary architecture of an HIS with an integrated image optimization module in accordance with some embodiments. As shown, the HIS 310 includes a MedServer 330, a PACS web server 340, a query object 350, a PACS 360, and an image optimization module 370 of some embodiments. The HIS 310 interfaces with one or more image acquisition devices 320 in order to acquire the images that populate the PACS 360 and client devices 325 that access the PACS 360 to retrieve the images for viewing.

The image acquisition devices 320 include any hospital imaging device (e.g., Magnetic Resonance Imaging (MRI) device, Computerized Axial Tomography (CAT) Scan device, etc.) used within the various wards or units of a hospital. Some examples of these various wards or units include radiology, cardiology, oncology, dentistry, surgery, neurology, mammography, radiotherapy, opthalmology, orthopedics, pediatrics, pathology, veterinary, etc. The image acquisition devices 320 are configured to operate using a single file format and network protocol standard. The following discussion uses the DICOM standard as the adopted standard with which the HIS is implemented. However, it should be apparent to one of ordinary skill in the art that any such file format and network protocol standard may be used in conjunction with the embodiments described herein. Therefore, when the devices 320 generate the images to send to the PACS 360, the devices 320 format the images according to the DICOM file format before transmitting the images to the MedServer 330.

The MedServer 330 is the primary server within the HIS that provides the interface between the image acquisition devices 320, the client devices 325, and the back-end components of the HIS, such as the PACS 360 and the image optimization module 370 as some examples. In some embodiments, the MedServer 330 performs authentication and/or authorization functionality for the image acquisition devices 320 and the client devices 325. In some embodiments, the MedServer 330 requests, organizes, and sends data to and from the image acquisition devices 320, the client devices 325, and the back-end components of the HIS.

Specifically, the MedServer 330 routes the various data and requests entering into the HIS 310 to the appropriate database, data storage, or computational unit of the HIS 310. For instance, when the MedServer 330 receives a newly generated image from an image acquisition device 320, the MedServer 330 identifies the image as a newly generated image to be stored in the PACS 360. Accordingly, the MedServer 330 routes the image to either the PACS web server 340 or query object 350 that represent contact points into the PACS 360.

In some embodiments, the MedServer 330 includes various scripts that implement the MedServer 330 functionality. For example, the MedServer 330 includes Hyper Text Transfer Protocol (HTTP) based scripts for interfacing with the PACS web server 340 that provides a web based interface into the PACS 360. The MedServer 330 may also include Component Object Model (COM) based scripts for interfacing with the query object 350 that provides a COM interface into the PACS 360. Other scripts may be implemented to compress images passing to the clients 325, to perform client authentication, to perform client authorization, etc.

By modifying one or more such scripts, the image optimization module 370 may be seamlessly integrated into the HIS. For instance, when the MedServer 330 receives a newly generated image from an image acquisition device 320 to be stored in the PACS 360, an image storage script of the MedServer 330 may be modified such that the image passes to the PACS 360 for storage and also to the image acquisition module 370 for optimization.

Similarly, when the MedServer 330 receives a request from a client to retrieve an image, an image retrieval script of the MedServer 330 may be modified to first query the image optimization module 370. If the image optimization module 370 has preprocessed and generated an optimized version of the requested image, then the image optimization module 370 returns the optimized image to the MedServer 330. The image retrieval script then returns the optimized image to the client submitting the request without querying the PACS 360.

If the preprocessed image does not exist, the image optimization module 370 notifies the MedServer 330 that the requested image has not been preprocessed. In some embodiments, the preprocessed image may not exist if it has been recently entered into the PACS 360 or if the requesting client has image settings for which the image optimization module 370 has not generated an optimized image. The image retrieval script then spawns a processing thread in the MedServer 330 that determines the PACS contact to be used (e.g., PACS web server 340 or query object 350). The MedServer 330 queries the PACS 360 to retrieve the original image. The original image is then optimized on-demand by the image optimization module 370 and stored in the database 380 as described in the Sections below. In some embodiments, the image retrieval script also spawns a monitoring thread. The monitoring thread continually checks the database 380 of the image optimization module 370 to determine when an optimized version of the requested image becomes available.

While the monitoring thread runs, the PACS 360 retrieves an original image that includes platform dependent formatting and that has not been optimized for the requesting client device. Before the original image is passed to the client 325 or the MedServer 330, the original image is processed on-demand by the image optimization module 370 such that the efficiency benefits gained from an optimized image may be realized irrespective of whether the image has been previously preprocessed by the image optimization module 370. Once the image optimization module 370 completes performing the one or more image optimization techniques, the image optimization module 370 updates the database 380 with the optimized image. The monitoring thread of the MedServer 330 then identifies the optimized image within the database 380. The monitoring thread retrieves the optimized image and forwards the optimized image to the requesting client 325.

FIGS. 4 and 5 present exemplary functions of a script that is processed by the MedServer 330 to retrieve a client requested image from the image optimization module 370 in accordance with some embodiments. Specifically, FIG. 4 presents a function for retrieving a single image study, whereas FIG. 5 presents a function for retrieving a study list that includes multiple images. Each of the functions initializes an object, 410 or 510, for submitting a DICOM query. Each of the functions also initializes an XML object, 420 or 520, for retrieving the results of the DICOM query. The XML object contains the platform independent formatted results of the query.

It should be apparent to one of ordinary skill in the art that the illustrated architectures of FIG. 3 detail a minimal set of components needed to implement some embodiments of the invention in an HIS. Therefore, the HIS may include additional components in addition to those illustrated in FIG. 3. Similarly, the image optimization module of some embodiments includes several components to implement the various preprocessing and optimization functionality.

Figure 6:
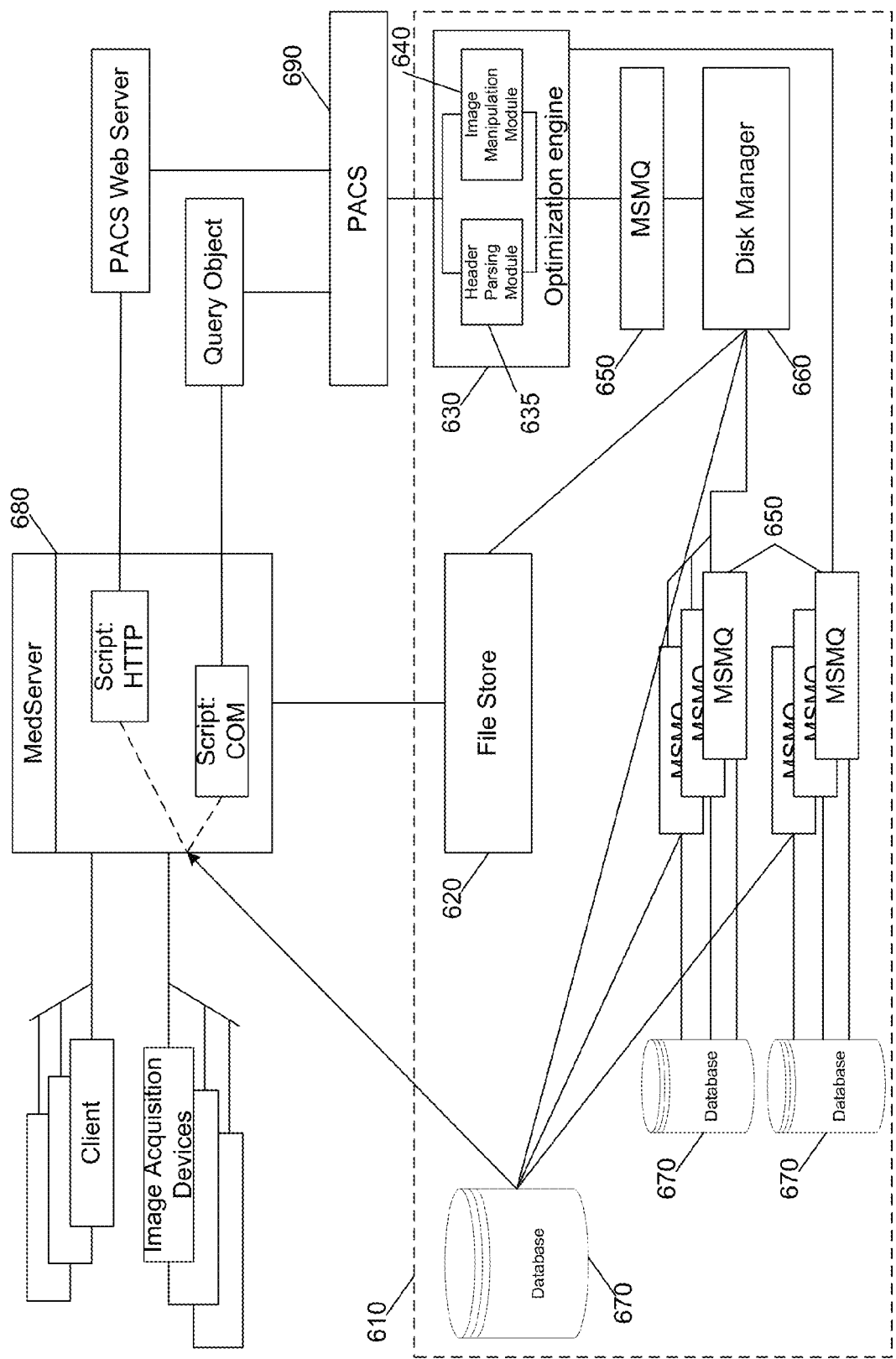
FIG. 6 illustrates some of the various components of an image optimization module of some embodiments.

FIG. 6 illustrates some of the various components of an image optimization module 610 of some embodiments. The image optimization module 610 includes a file store 620, an optimization engine 630, a set of messaging queues 650, a disk manager 660, and a set of databases 670.

The file store 620 stores identifiers to preprocessed images of the image optimization module 610 that are stored within the set of databases 670. In some embodiments, the identifiers include platform independent header information of the preprocessed images. In some embodiments, the identifiers are pointers to the images within the set of databases 670.

For example, the file store 620 includes headers or pointers for an original image with a resolution of 2560×1980 pixels that has been preprocessed to generate optimized images. The optimized images are stored in the databases 670 where the optimized images have a 800×600 pixel resolution and a 640×480 pixel resolution. Therefore, if a particular device has a display resolution of 800×600 pixels and requests the original image, the MedServer 680 is able to determine from the file store 620 that a preprocessed image optimized for the particular device exists within the set of databases 670. In some embodiments, the MedServer 680 is provided with a pointer into the set of databases 670. Using the pointer, the MedServer 680 retrieves the appropriate optimized image. In some embodiments, the image optimization module automatically passes the appropriate optimized image for the particular device from the databases 670 to the MedServer 680 once the status is determined from the file store 620.

Should the requesting device have a resolution for which an optimized image does not exist (e.g., 1280×768 pixels), then image quality of the original image will be lost using any one of the preprocessed images stored in the file store 620. Accordingly, the MedServer 680 determines from the file store 620 that an optimized image for the requested image does not exist. The MedServer 680 then reroutes the query to the PACS 690. The PACS 690 retrieves the original image. The optimization engine 630 receives the retrieved original image and performs an on-demand optimization of the image. The optimized result is then passed to the requesting device. Additionally, the optimization engine 630 stores the optimized image to the database 670 such that the image optimization engine 630 does not have to reperform the on-demand optimization for a subsequent request for the image.

In some embodiments, the optimization performed by the optimization engine 630 is configurable based on one or more XML configuration files. In some embodiments, the configuration specifies the various optimization modules for the optimization engine 630. In this manner, the configuration file specifies the optimizations to apply to the image. For purposes of simplicity only two such optimization modules, modules 635 and 640, are shown. However, it should be apparent to one of ordinary skill in the art that any number of additional optimization modules may be added to or used to replace the modules 635 and 640. For instance, in some embodiments, the optimization engine 630 includes a compression module to compress the optimized images.

By using the various optimization modules, the optimization engine 630 of some embodiments includes multiple image processing paths. Each path may perform a certain image optimization procedure in parallel with another path. In this manner, the image optimization module 610 is able to simultaneously perform header manipulation along a first path that is executed by the header parsing module 635 and image processing along a second path that is executed by the image manipulation module 640.

Figure 7:
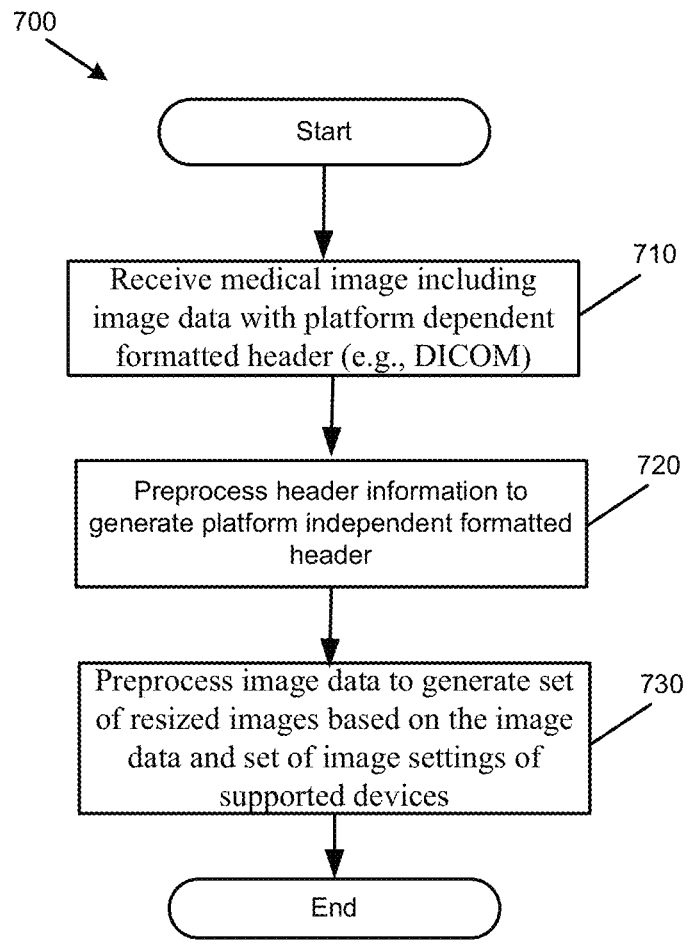
FIG. 7 presents a process performed by the optimization modules of the optimization engine in accordance with some embodiments.

FIG. 7 presents a process 700 performed by the optimization modules of the optimization engine 630 in accordance with some embodiments. The process begins by receiving (at 710) an image that includes a header that is formatted in a platform dependent format, such as a DICOM format. In some embodiments, the headers provide descriptive information about the image such as the encoding or type of the image (e.g., bitmap, Joint Photographic Experts Group (JPEG), Graphics Interchange Format (GIF), etc.), the image dimensions or resolution, the amount of image content (e.g., size in bytes), and other descriptive metadata. Without being able to decode the header, an application or client device is unable to display the image properly.

The process then preprocesses the DICOM file header to generate a platform independent file header, such as XML. In this manner, any device with XML capabilities will be able to parse the file and therefore render the image even though the image was originally formatted to adhere to the DICOM standard. In some embodiments, the header parsing module 635 of the optimization engine 630 performs the header formatting conversion. A more detailed discussion of the header format conversion is provided in Section III below.

The process then performs one or more additional optimizations. For instance, the process preprocesses the image data to generate (at 730) a set of resized images based on the original image data. In some embodiments, the image manipulation module 640 performs the image resizing in order to optimize the image data for one or more different display parameters (e.g., resolution, color depth, etc.). In some embodiments, the original image is resized by down sampling the original image to a lower resolution that matches the display resolution of a display device requesting the image. Less data then needs to be transmitted to the device when transmitting the resized image instead of the original image. Additionally, the down sampling results in no quality loss as the down sampling reduces the dimensions of the original image to match those of the display settings of the requesting client device. A more detailed discussion of the image optimizations is provided in Section IV below.

Figure 8:
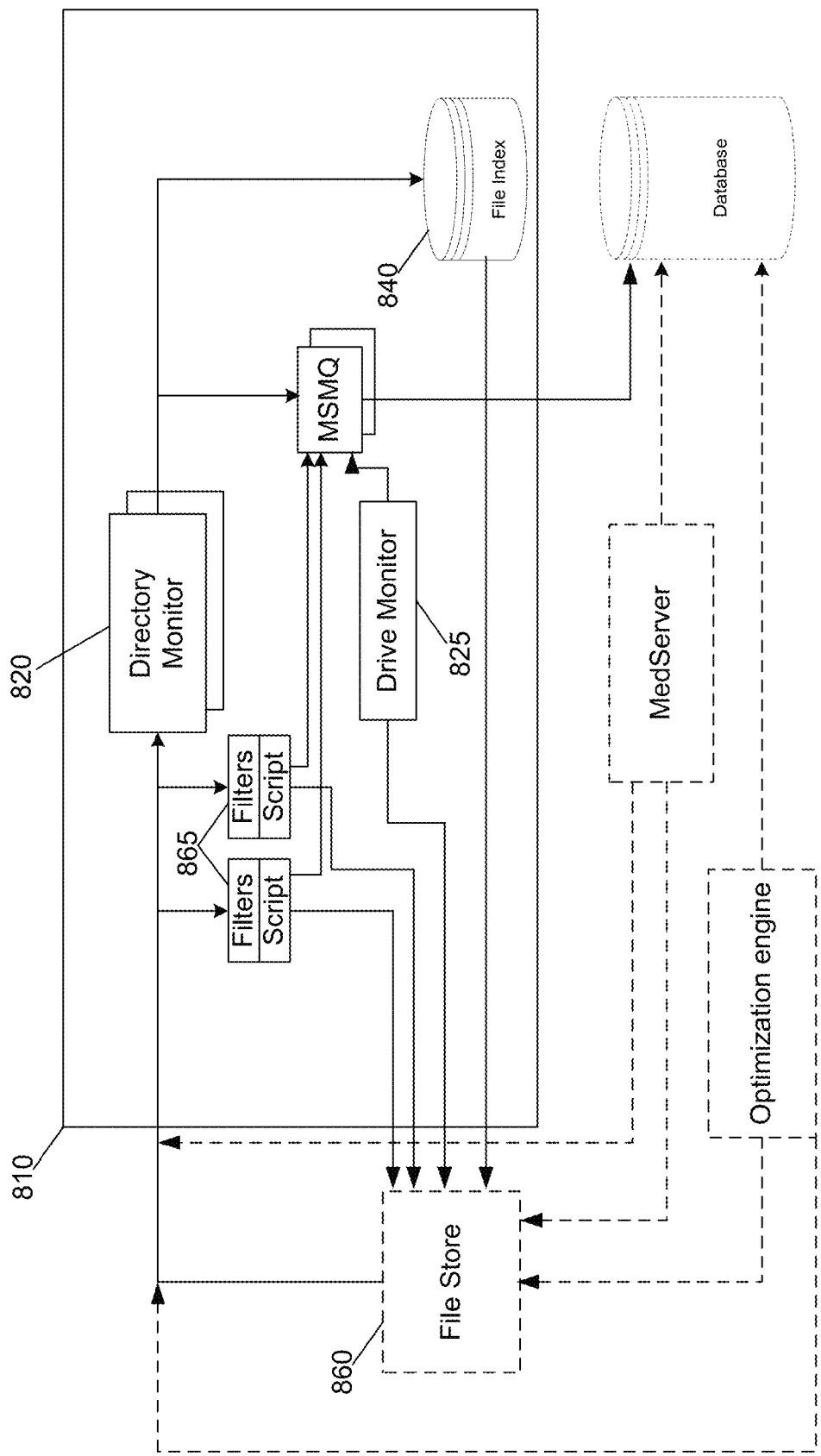
FIG. 8 conceptually illustrates a disk manager in accordance with some embodiments.

Once the image header has been converted and the image data optimized, the disk manager 660 of FIG. 6 is tasked with storing the preprocessed or on-demand generated data within the file store 620 and with populating the database 675. FIG. 8 conceptually illustrates a disk manager 810 in accordance with some embodiments. The disk manager 810 includes a directory monitor 820, a drive monitor 825, and a file index 840.

In some embodiments, the directory monitor 820 in conjunction with or independent of the drive monitor 825 periodically checks the status of the file store 860. Specifically, the directory monitor 820 triggers cleanup of the file store 860 when usage of the file store 860 (e.g., resource levels and utilization levels) reaches or exceeds a threshold. In some embodiments, the directory monitor 820 triggers cleanup when it is detected that an image has been updated, modified, or deleted from the PACS. Such actions render all previously preprocessed data obsolete, thereby necessitating the removal of such preprocessed images from the image optimization module. The image optimization module will then have to generate a new set of preprocessed images for the modified or updated image. In some embodiments, the directory monitor 820 utilizes one or more filters and scripts 865 to perform the monitoring and cleanup.

In some embodiments, the directory monitor 820 performs cleanup of the file store 860 based on notifications received from the optimization engine or from the MedServer. In some embodiments, the optimization engine or the MedServer instructs the file store 860 to create or modify resources using one or more of the filters 865. The filters 865 identify filenames and extensions of images or files to process. When a filter's criteria are met, the script that is associated with the filter is executed. The script specifies the actions to perform on the files.

The file index 840 contains a map of the folders, folder sizes, file sizes, access times, files, etc. The monitors 820 and 825 initially create the index at startup and the file index 840 is updated as messages are processed.

With reference to FIG. 6, the various messaging queues 650 temporarily retain the messages passing within the image optimization module 610 until the messages are processed by the appropriate module. For instance, a messaging queue 650 may be used to retain a set of preprocessed results as the images are passed to the disk manager 660 for storage within the file store 620 and other databases 670.

It should be apparent to one of ordinary skill in the art that the image optimization module of some embodiments is dedicated hardware, such as a computer, with memory and processing resources to perform the various preprocessing and optimization functionality described above and further detailed below. In some embodiments, the image optimization module of some embodiments is defined using a set of computer readable software instructions that are executed by hardware components of an HIS. In this manner, the image optimization module may be integrated with existing components of the HIS or may be integrated into the HIS with newly deployed hardware. For example, the image optimization module of some embodiments is a plug-in module that provides additional functionality to the PACS.

III. Preprocessing of the Image Header

In some embodiments, the image optimization module increases the usability of the PACS while reducing the cost associated with the increased usability of the PACS. One manner by which the image optimization module realizes such benefits is by removing the platform dependencies that exist in a typical PACS. Such dependencies are commonly introduced in an effort to ensure a common and compatible format for medical images of an HIS. Specifically, these dependencies ensure a common and compatible format between the various different image acquisition devices that acquire and generate the image files and the client devices that access and view the acquired image files. DICOM is one example of a platform dependent file format that has emerged as a standard for formatting medical images in an HIS.

To encode or decode according to the DICOM format requires the encoding or decoding device to have the necessary DICOM libraries. The DICOM libraries define the DICOM image file format for generating and viewing a DICOM formatted image file. The DICOM libraries also define the communication protocols for sending and receiving DICOM formatted image files from one DICOM compliant device to another. However, these platform dependencies have restricted the use of medical images and PACS to a specialized set of DICOM compliant devices that include the DICOM libraries. These DICOM compliant devices increase the costs for health care providers and hospitals. Specifically, medical personnel carry one set of devices for communicating within the hospital such as pagers, smartphones, or PDAs and another set of devices for accessing the platform dependent images stored in the PACS. This is because many of the communication devices carried by the medical personnel either do not support the DICOM platform or would incur substantial licensing costs to enable each of the communication devices to support the DICOM platform.

The image optimization module of some embodiments removes the need for such specialized devices by replacing the platform dependent file format with a platform independent file format. Specifically, by removing the platform dependencies, the communication devices generally carried by medical personnel (e.g., smartphones, PDAs, etc.) no longer have to adhere to the platform dependencies of the DICOM format and thus no longer need to incur the licensing costs associated with supporting the platform dependent format. Furthermore, the devices are no longer burdened with the processing and memory overhead required for storing the DICOM libraries and decoding the DICOM format locally on the client device. This allows any number of platform independent devices to view the images and access the functionality of the PACS. As a result, the overall cost to the healthcare provider or hospital is reduced as images that are stored within the PACS may be disseminated to medical personnel using generally available communication devices already within the possession of most medical personnel without requiring change or upgrades to such devices.

Figure 9:
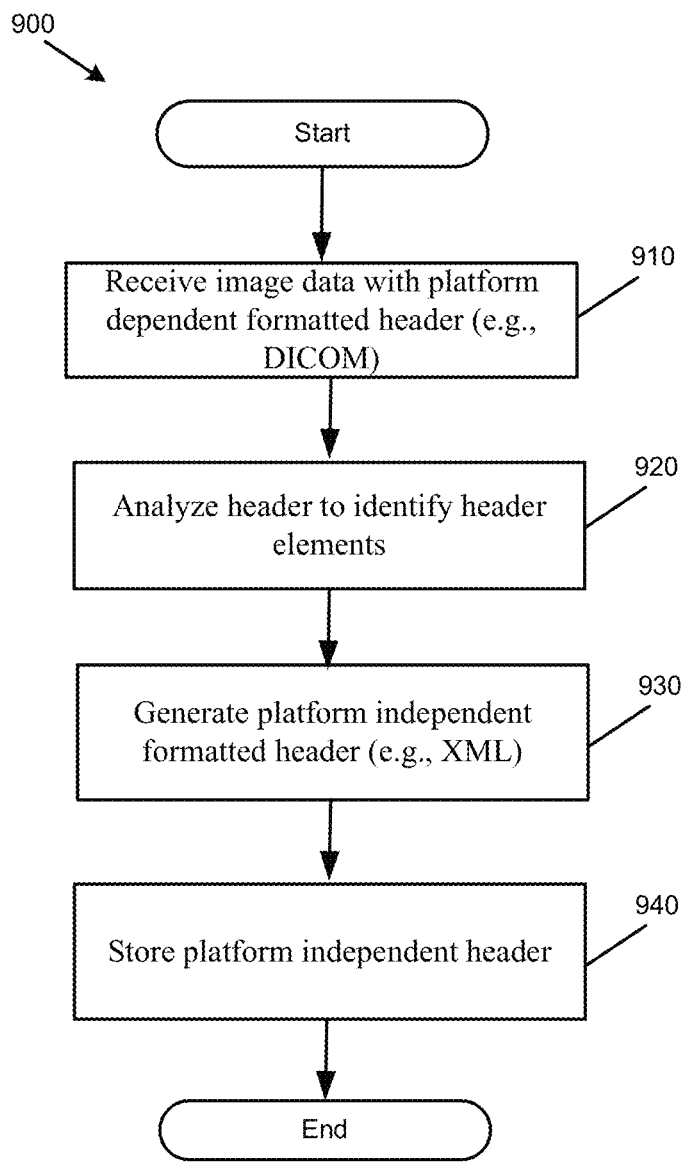
FIG. 9 presents a preprocessing process for optimizing an image for efficient transfer to a client device in accordance with some embodiments.

FIG. 9 presents a preprocessing process 900 for converting an image file that is formatted in a platform dependent format to platform independent format for viewing on a client device in accordance with some embodiments. The process 900 commences by receiving (at 910) a medical image that is formatted according to a platform dependent file format such as DICOM. Specifically, the file format includes a platform dependent formatted header that describes the contents of the file and the specifications of the image. Therefore, in order to properly view the image, a client device or application must first decode the header in order to determine the image contents. In some embodiments, process 900 begins and specifically step 910 occurs when an image is received by the PACS or when the image is received by the MedServer.

The process analyzes (at 920) the platform dependent file format using one or more libraries that define and encode or decode the format. As part of the analysis, the process identifies the various elements of the header that contain the descriptive information for the associated image data. As noted above, these header elements may include the image type, resolution, size, etc.

In order to generate the platform independent file format, the process generates (at 930) a platform independent formatted header that contains the same or similar information as the platform dependent formatted header. In some embodiments, the platform independent format specifies an XML formatted header for the image. In some embodiments, the process generates (at 930) several different XML formatted headers for the same image. Each such formatted header corresponds to attributes of a different resized image that are or will be generated for the received image.

The process stores (at 940) the resulting platform independent header information. Some embodiments store the platform independent header information separately from the image data in the file store 620 of FIG. 6. The XML header is used as a pointer to identify and retrieve the actual image content from the one or more databases 670 that store the corresponding image data. By storing only the header information in the file store, subsequent searches into the file store will be performed with lower latency as only the image header information is searched as opposed to searching the header information and the image content.

FIG. 10 illustrates contents of a DICOM formatted header that has been converted to an XML formatted header 1005 in accordance with some embodiments of the invention. The XML formatted header 1005 is representative of header information that is stored within the file store 620. As shown, the data is demarcated with a set of XML tags. Each tag provides some descriptive information about the image. For example, tag 1010 describes the image as a MRI brain scan and tag 1020 provides the name of the patient for whom the image belongs.

A benefit of the XML formatted header 1005 is that powerful and efficient SQL queries may be used to search through the image content. Conversely, DICOM formatted headers require proprietary search engines that underperform when compared against established SQL search engines. Moreover, any tag in the XML formatted header 1005 may be used as a searchable attribute. In this manner, the functionality of the PACS is expanded such that customized queries may be performed over the set of images, where such customized queries would otherwise be unavailable when querying data that is formatted in the DICOM file format. For instance, users may search images for a particular patient based on the patients name tag 1020 and more sophisticated queries may be specified whereby images for a particular patient's name that were generated after a specific date may be queried using the patient's name tag 1020 and the study date tag 1030. It should be apparent to one of ordinary skill in the art that any combination of tags may be used to specify queries that identify images.

FIG. 11 illustrates pseudo-code 1100 for converting a DICOM formatted header to a XML formatted header. The pseudo-code operates as a loop 1110 that traverses each node of the DICOM formatted header where a node specifies a set of demarcated data within the DICOM file format. The pseudo-code analyzes and extracts value representations (VRs) from the node. Some embodiments represent the value representations as strings within the XML format. Some embodiments omit certain value representations such as an "OB" type that represents image data.

Additionally, some DICOM header nodes include sequenced tags. A sequence tag represents a tag that is nested within other tags. When processing a value representation with a sequence tag, the pseudo-code determines the number of sequenced tags of the value representation. This value multiplicity (VM) value specifies the number of sequenced tags. Accordingly, these tags are grouped together when performing the XML conversion. As shown in FIG. 10, the tags 1040 represent a sequenced tag with a value multiplicity of three.

Some embodiments compress the resultant XML formatted header. By performing the compression, the amount of information that is transferred to the client device is reduced. As a result, less bandwidth is needed to transfer the information and the transfer occurs with lower latency. In some embodiments, the client requests compression when requesting an image. For instance, the user may request Z-Lib compression when requesting an image. It should be apparent to one of ordinary skill in the art that even though FIGS. 9-11 and other figures have been described with respect to converting a DICOM formatted header to an XML formatted header, the techniques similarly apply to the conversion of any platform dependent format to a platform independent format.

IV. Preprocessing of the Image

In some embodiments, the image optimization module increases the usability of the PACS by optimizing the image content that is transferred to a client device. In some such embodiments, the image optimization module optimizes the image content by down sampling the image based on image display settings of the client device. Such down sampling resizes the image by reducing the image size without reducing the quality of the image. For instance, an original image having a resolution 2560×1980 down sampled and resized to 640×480 will have no quality loss when displayed on a display device that has a maximum resolution of 640×480.

As a result, the image optimization module of some embodiments transfers image content more efficiently than the PACS. For instance, the PACS sends original image content using the full set of pixel data of the original image whereas the image optimization module reduces the amount of pixel data that is sent to the client device based on the display capabilities of the client device. In this manner, extraneous pixel data that would otherwise be excluded in the displayed image is not unnecessarily sent to the client device. The image optimization module transfers less image data without impacting the image quality on the client device. Accordingly, the image optimization module transfers images to a client device faster and with lower latency than the PACS.

A further benefit of the image optimization performed by some embodiments is that the client device has to do less processing in order to display the image. Firstly, less pixel data is sent to the client device, therefore the client device has less data to process in order to display the image. Secondly, since the image is already optimized for the screen display of the client device, the client device does not need resample the image (e.g., down sample or up scale the image resolution) in order to display the image. Accordingly, the client device is able to display the image faster using fewer processing and memory resources. This allows less powerful devices to still be able to view the images.

In some embodiments, the down sampling preprocessing performed by the image optimization module occurs in conjunction with the header conversion preprocessing described in the Section above. In some other embodiments, the down sampling is a batch process that runs at specified intervals.

Figure 12:
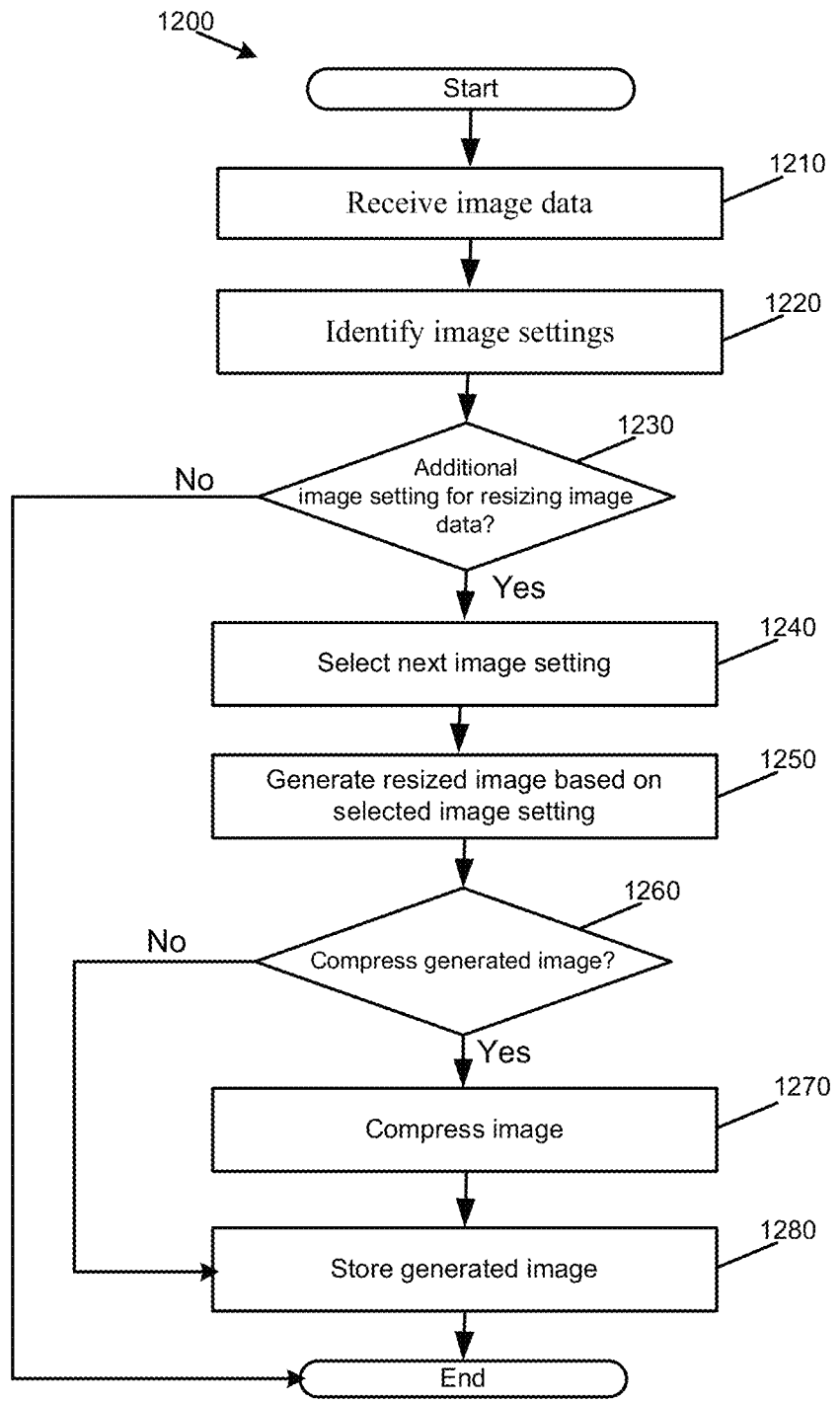
FIG. 12 presents a process performed by the image optimization module of some embodiments to optimize an image for the efficient transfer of the image to a client device.

FIG. 12 presents a process 1200 performed by the image optimization module of some embodiments to optimize an image for the efficient transfer of the image to a client device. The process 1200 begins by receiving (at 1210) an image. In some embodiments, the process receives the image when the image is transferred from an image acquisition device to the PACS for storage. In some such embodiments, the image optimization occurs as part of the preprocessing performed by the image optimization module. In some other embodiments, the process receives the image as part of a client device requesting retrieval of the image from the PACS. In some such embodiments, the image optimization occurs on demand as part of image transfer.

The process then identifies (at 1220) one or more image settings that define the one or more resized images that are to be generated. Some embodiments predetermine one or more image display settings that define the one or more down sampled versions of the image to generate during preprocessing. Additionally, when the image optimization module identifies a request for an image that is sent by a client device having image display settings different from the predetermined settings, the image optimization module of some embodiments identifies the image display settings on-demand based on the particular image display settings of the requesting client device. In this manner, the image optimization module of some embodiments generates an on-demand down sampled image that is down sampled according to the particular image display settings of the requesting client device.

After identifying (at 1220) the one or more image settings, the process determines (at 1230) whether to generate a resized image based on the identified settings. If the process determines (at 1230) that it has generated resized images for all identified image display settings, the process ends. Otherwise, the process selects (at 1240) an identified image display setting in order to generate the corresponding resized image. The process then generates (at 1250) the corresponding resized image based on the selected down sampling image display settings.

In some embodiments, the process performs additional image optimization. One such image optimization technique is to compress the image data such that less data is transferred from the image optimization module to the client. By combining image compression with the image down sampling of step 1250, the process is able to realize even further image optimization gains. These optimization gains reduce bandwidth requirements and lower latency when compared to transferring the original image that is not down sampled or compressed from the PACS to the client device. Compression therefore allows for the image to be transferred to the client device faster at the cost of having to decompress the image locally on the client device. Accordingly, the process determines (at 1260) whether to compress the resized image. If no compression is performed, the process stores (at 1280) the generated resized image. Otherwise, the process compresses (at 1270) the image before storing (at 1280) the resized and compressed image.

Some embodiments utilize standard compression algorithms to compress the image. For instance, some embodiments utilize various levels of JPEG compression, Z-Lib compression, Wavelet compression, or PNG compression as some examples. In some embodiments, the client specifies the types of compression that the client device is able to support from which the image optimization module determines whether to perform the compression.

In some embodiments, the process stores the generated images within the databases 670 of FIG. 6. A pointer to these images is provided in the file store 620. The pointer is associated with the platform independent headers of the generated images.

Figure 13:
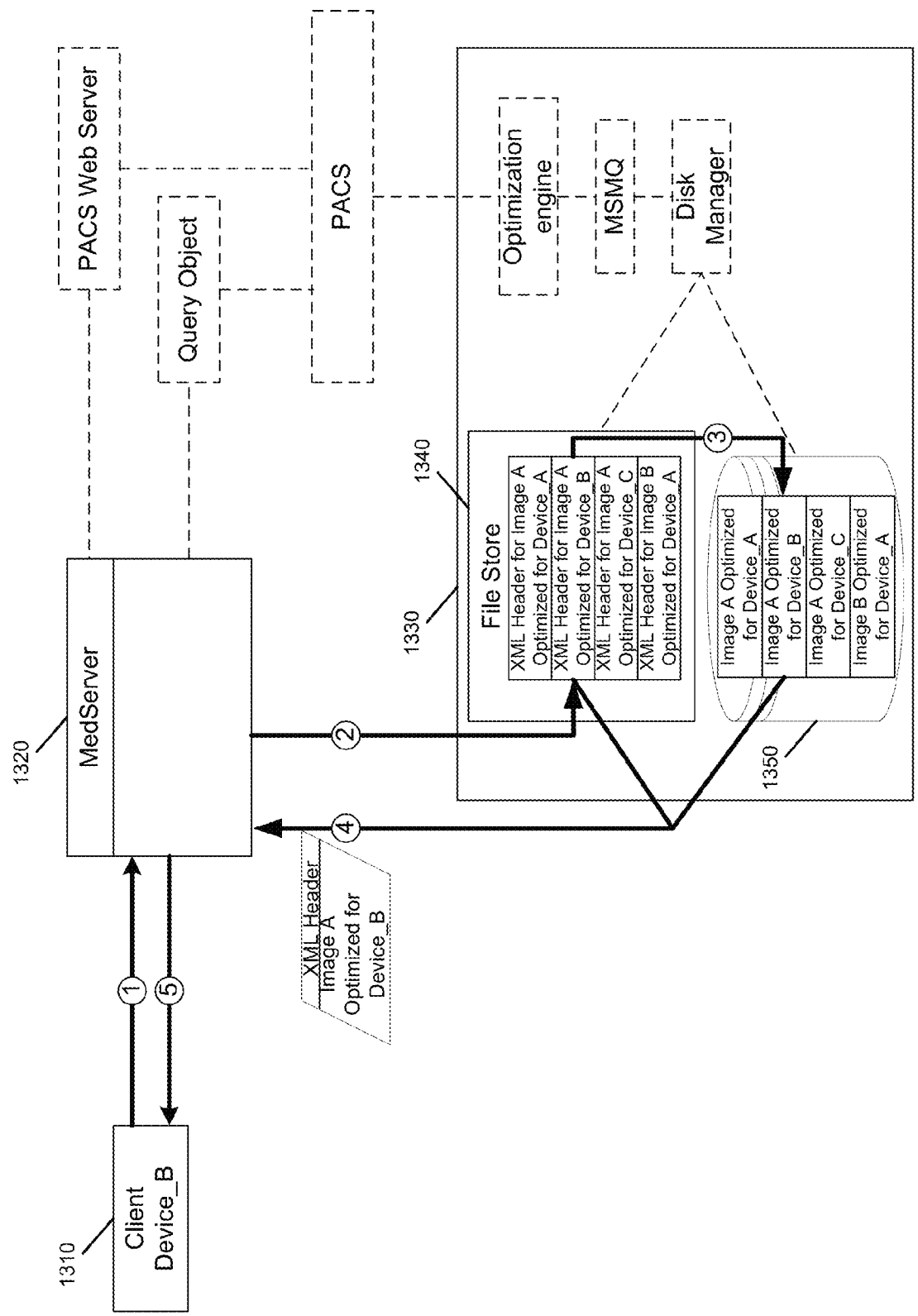
FIG. 13 conceptually illustrates a data flow for transferring a preprocessed optimized image from an HIS to a client device.

FIG. 13 conceptually illustrates a data flow for transferring a preprocessed optimized image from an HIS to a client device. For purposes of simplicity, this figure illustrates a simplified version of the HIS system architecture presented in FIG. 6. Additionally, only the components involved in the data flow are illustrated with solid lines. These components include a client device 1310, a MedServer 1320, an image optimization module 1330 of some embodiments, a file store 1340 of the image optimization module 1340, and at least one database 1350 of the image optimization module 1340.

The client device 1310 submits an initial request, represented by the encircled number 1, to retrieve image content from the HIS. The MedServer 1320 receives the image request. Rather than query a PACS to retrieve the original image that is not optimized for display on the client device 1310, the MedServer 1320 submits the request to the image optimization module 1330. Specifically, the request passes to the file store 1340 of the image optimization module 1330.

The image optimization module 1330 identifies image display settings of the client device 1310 submitting the request. Based on these identified parameters, the image optimization module 1330 identifies a header within the file store 1340 that corresponds to a preprocessed version of the requested image optimized for display on the client device 1310. Specifically, the image optimization module 1330 utilizes the identified header as a pointer into the database 1350. The image optimization module 1330 then retrieves the corresponding image data for the identified header from the database 1350. The image optimization module then passes the optimized image to the MedServer 1320. The MedServer 1320 receives the optimized image and forwards the optimized image to the client 1310.

Figure 14:
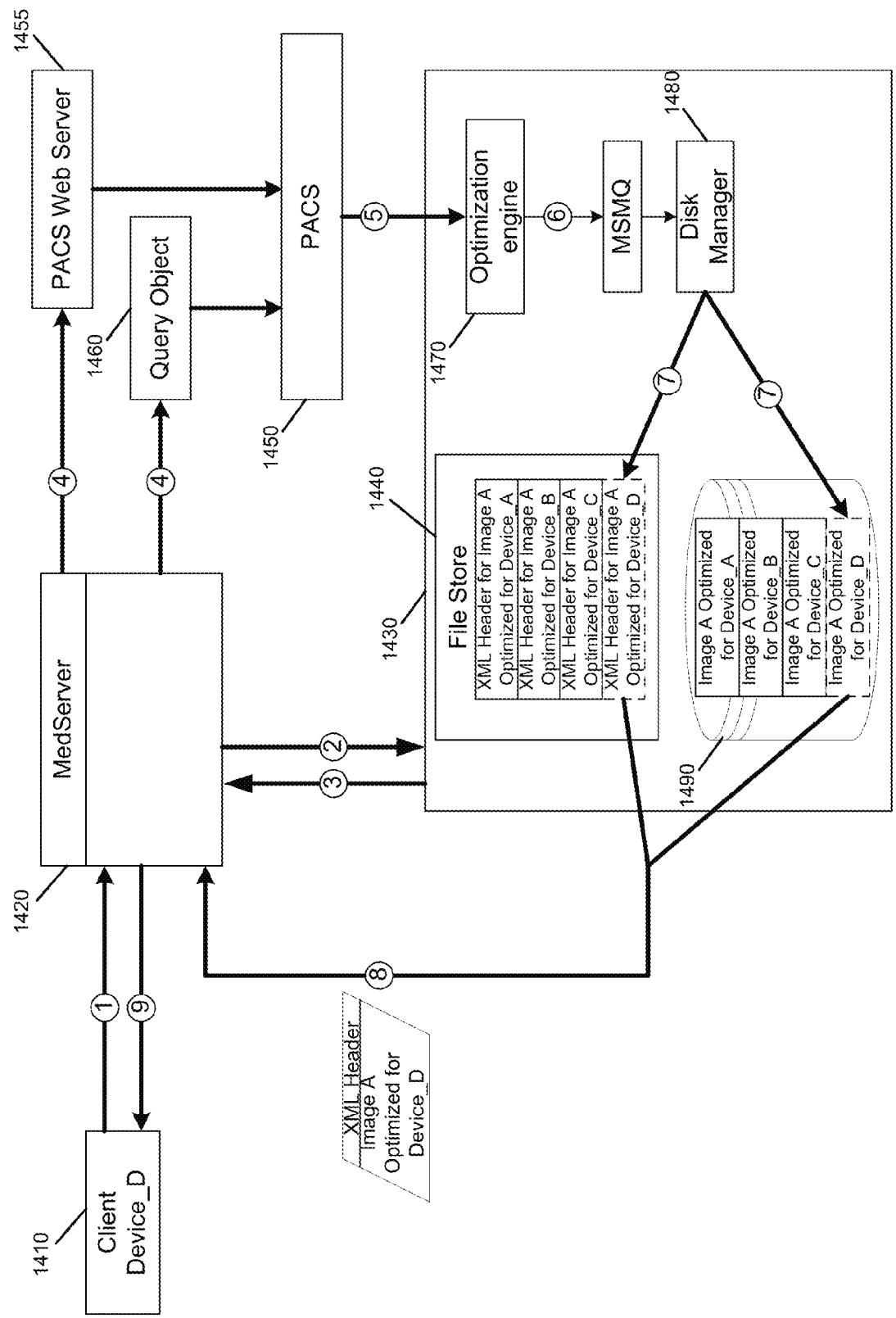
FIG. 14 conceptually illustrates a data flow for transferring an image that is optimized on-demand from an HIS to a client device.

FIG. 14 conceptually illustrates a data flow for transferring an image that is optimized on-demand from an HIS to a client device. As before, the client device 1410 submits a query to the MedServer 1420 to commence the image retrieval process. The MedServer 1420 again submits the query to the image optimization module 1430 to determine whether an optimized version of the image has been preprocessed. However in this scenario, the file store 1440 does not contain the necessary pointer information to indicate that the optimized image has not been preprocessed. Accordingly, the image optimization module 1430 notifies the MedServer 1420 that an optimized version of the image does not exist. An optimized image may not exist for certain image display settings of client devices that are not within a predetermined set of image display settings. It should be apparent to one of ordinary skill in the art that various other reasons may exist that necessitate the on-demand image optimization process.

The MedServer 1420 then forwards the request to the PACS 1450 using either the PACS web server 1455 or the query object 1460. The PACS 1450 retrieves the original version of the image that has not been optimized for display on any particular client device. Additionally, the original version of the image in many instances is stored with the platform dependent header information. Accordingly, the optimization engine 1470 identifies the retrieval of the image from the PACS 1450. The optimization engine 1470 also identifies that the image should be optimized before transmission to the client device 1410. The optimization engine then performs the on-demand image optimization process.

In some embodiments, the on-demand optimization performs the platform dependent to platform independent header conversion, down samples the image, and/or performs data compression. In some embodiments, the data compression involves compressing the converted header, the original image content, the down sampled image content, the converted header and the original image content, or the converted header and the down sampled image content.

The optimization engine 1470 then notifies the disk manager 1480 to ensure that sufficient space exists within the file store 1440 and the database 1490 to store the optimized image. Once complete, the optimized image information is queued within the file store 1440 and the database 1490 and the optimized image is transferred from the image optimization module 1430 to the MedServer 1420. The MedServer 1420 then routes the optimized image to the client device 1310 for display.

V. Computer System

Many of the above-described components (e.g., MedServer, image optimization module, optimization engine, etc.) implement some or all the above described functionality through software processes that are specified as a set of instructions recorded on a machine readable medium (also referred to as computer readable medium). When these instructions are executed by one or more computational element(s) (such as processors or other computational elements like ASICs and FPGAs), they cause the computational element(s) to perform the actions indicated in the instructions. Computer is meant in its broadest sense, and can include any electronic device with a processor. Examples of computer readable media include, but are not limited to, CD-ROMs, flash drives, RAM chips, hard drives, EPROMs, etc.

In this specification, the term "software" is meant in its broadest sense. It can include firmware residing in read-only memory or applications stored in magnetic storage which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention.

Figure 15:
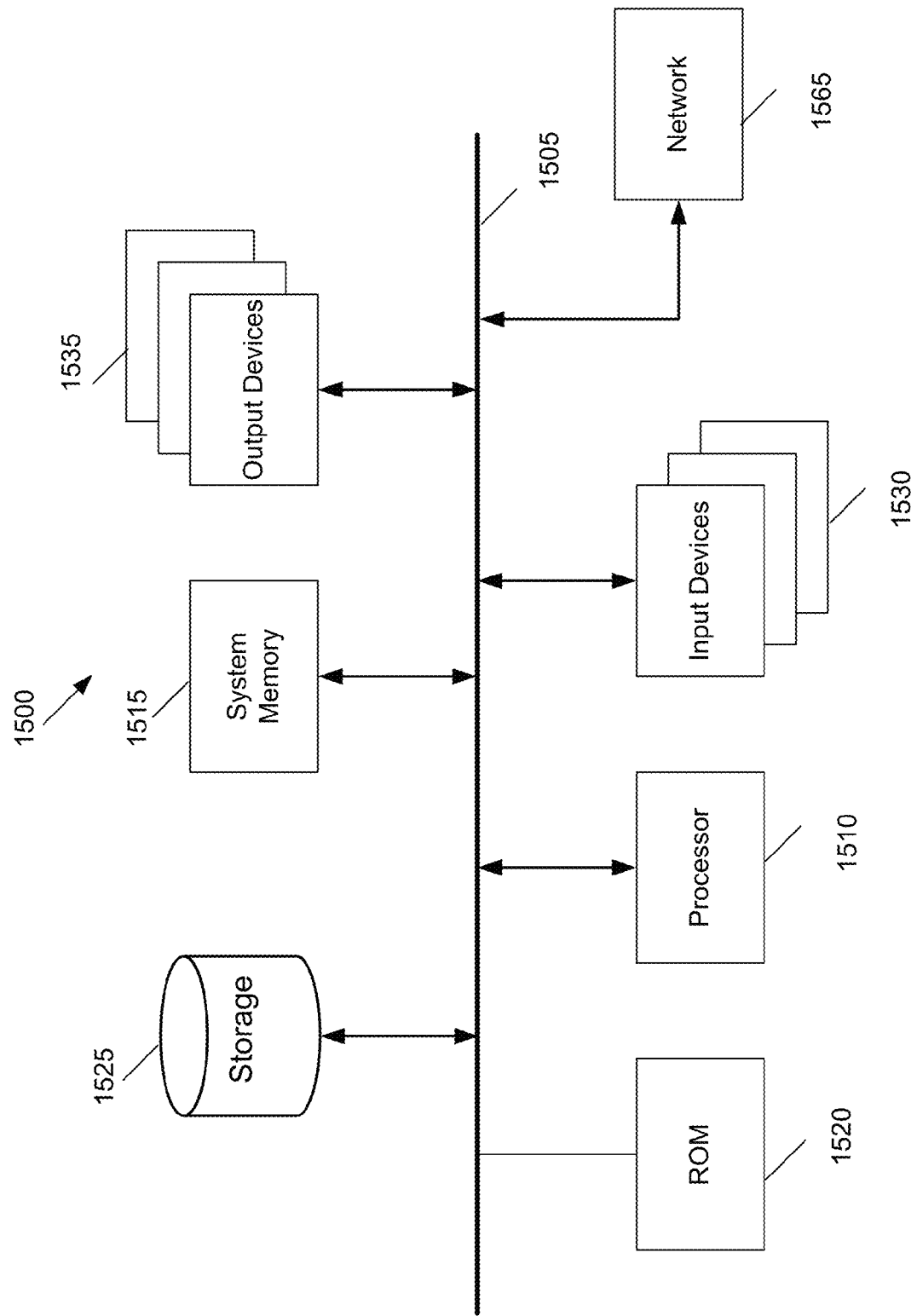
FIG. 15 conceptually illustrates a computer system with which some embodiments of the invention are implemented.

FIG. 15 illustrates a computer system with which some embodiments of the invention are implemented. Such a computer system includes various types of computer readable mediums and interfaces for various other types of computer readable mediums. Computer system 1500 includes a bus 1505, a processor 1510, a system memory 1515, a read-only memory 1520, a permanent storage device 1525, input devices 1530, and output devices 1535.

The bus 1505 collectively represents all system, peripheral, and chipset buses that communicatively connect the numerous internal devices of the computer system 1500. For instance, the bus 1505 communicatively connects the processor 1510 with the read-only memory 1520, the system memory 1515, and the permanent storage device 1525. From these various memory units, the processor 1510 retrieves instructions to execute and data to process in order to execute the processes of the invention.

The read-only-memory (ROM) 1520 stores static data and instructions that are needed by the processor 1510 and other modules of the computer system. The permanent storage device 1525, on the other hand, is a read-and-write memory device. This device is a non-volatile memory unit that stores instructions and data even when the computer system 1500 is off. Some embodiments of the invention use a mass-storage device (such as a magnetic or optical disk and its corresponding disk drive) as the permanent storage device 1525.

Other embodiments use a removable storage device (such as a floppy disk, flash drive, or ZIP® disk, and its corresponding disk drive) as the permanent storage device. Like the permanent storage device 1525, the system memory 1515 is a read-and-write memory device. However, unlike storage device 1525, the system memory is a volatile read-and-write memory, such a random access memory (RAM). The system memory stores some of the instructions and data that the processor needs at runtime. In some embodiments, the invention's processes are stored in the system memory 1515, the permanent storage device 1525, and/or the read-only memory 1520.

The bus 1505 also connects to the input and output devices 1530 and 1535. The input devices enable the user to communicate information and select commands to the computer system. The input devices 1530 include alphanumeric keyboards and pointing devices (also called "cursor control devices"). The input devices 1530 also include audio input devices (e.g., microphones, MIDI musical instruments, etc.). The output devices 1535 display images generated by the computer system. For instance, these devices display a GUI. The output devices include printers and display devices, such as cathode ray tubes (CRT) or liquid crystal displays (LCD).

Finally, as shown in FIG. 15, bus 1505 also couples computer 1500 to a network 1565 through a network adapter (not shown). In this manner, the computer can be a part of a network of computers (such as a local area network ("LAN"), a wide area network ("WAN"), or an Intranet, or a network of networks, such as the internet.

As mentioned above, the computer system 1500 may include one or more of a variety of different computer-readable media. Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ZIP® disks, read-only and recordable blu-ray discs, any other optical or magnetic media, and floppy disks.

It should be recognized by one of ordinary skill in the art that any or all of the components of computer system 1500 may be used in conjunction with the invention. For instance, some or all components of the computer system described with regards to FIG. 15 comprise some embodiments of the image optimization module, MedServer, optimization engine, etc. described above. Moreover, one of ordinary skill in the art will appreciate that any other system configuration may also be used in conjunction with the invention or components of the invention. Thus, one of ordinary skill in the art would understand that the invention is not to be limited by the foregoing illustrative details, but rather is to be defined by the appended claims.

What is claimed is:

1. A method for transferring medical images through an image optimization module from a Picture Archiving and Communication System (PACS) to one or more different display devices, the method comprising:
    receiving a medical image in a first platform dependent format of the Picture Archiving and Communication System (PACS) that is accessible by a first format compliant device, the first format compliant device comprising platform dependent resources for decoding said first format;
    receiving a request for the medical image for viewing on a second format compliant device having one or more image display settings;
    searching, in response to the request, a file store in the image optimization module for a header associated with the medical image in the second format;
    if a header for the medical image in the second format is found in the file store:
        retrieving the medical image in the second format from a database in the image optimization module; and
        passing the medical image in the second format to the second format compliant device;
    if a header for the medical image in the second format is not found in the file store:
        transforming the medical image on the image optimization module from the first format to the second format based on the one or more image display settings of the second format compliant device;
        generating a header associated with the medical image in the second format;
        passing the medical image in the second format to the second format compliant device for viewing;
        storing, in the database in the image optimization module, the medical image in the second format; and
        storing the generated header in the file store.

2. The method of claim 1, wherein the step of transforming comprises down sampling the medical image based on image display settings of the second format compliant device.

3. The method of claim 1, further comprising the step of, if a header for the medical image in the second format is not found in the file store, compressing the medical image in the second format before passing it to the second format compliant device.

4. The method of claim 1, further comprising the step of, if a header for the medical image in the second format is not found in the file store, first retrieving the medical image in the first format from the PACS.

5. The method of claim 1, wherein the step of receiving a medical image in a first platform dependent format comprises receiving a plurality of medical images in the first platform dependent format; and the method further comprising:
    identifying a plurality of known image settings corresponding a plurality of devices that display medical images;
    transforming each of the plurality of received medical images from the first format to a plurality of transformed medical images having formats corresponding to the plurality of known image settings;
    generating a header for each transformed medical image;
    storing each transformed medical image in the database of the image optimization module; and
    storing each generated header in the file store.

6. The method of claim 1, wherein passing the transformed medical image comprises passing image data associated with the transformed medical image and the generated header to the second format compliant device.

7. The method of claim 1, wherein the second format compliant device does not include the platform dependent resources for decoding the first format.

8. The method of claim 1, wherein the second format compliant device comprises a standard browser for viewing the transformed image that is passed to the device.

9. The method of claim 1, wherein the second format compliant device comprises a standard image viewing application for viewing the transformed image that is passed to the device.

10. The method of claim 1, wherein the first format is the Digital Imaging and Communications in Medicine (DICOM) format.

11. The method of claim 10, wherein the second format is the Extensible Markup Language (XML) format.

12. The method of claim 1, wherein said step of passing the transformed medical image comprises passing less data than passing the medical image in the first format.

13. A system for transferring medical images from a Picture Archiving and Communication System (PACS) to one or more different display devices, comprising:
  an image store containing a plurality of digital medical images in a first format; and
  an image optimization device communicatively coupled to the image store, comprising:
    a file store;
    one or more databases
    one or more processors; and
    software stored in the device for execution by the one or more processors for:
      receiving a request for one of the plurality of digital medical images for viewing on a second format compliant device having one or more image display settings;
      searching, in response to the request, the file store for a header associated with the requested medical image in the second format;
      retrieving the requested medical image in the second format from the one or more databases if a header for the requested medical image in the second format is found in the file store;
      retrieving the requested medical image from the image store if a header for the requested medical image in the second format is not found in the file store;
      transforming the requested medical image from the first format to the second format based on the one or more image display settings of the second format compliant device;
      generating a header associated with the requested medical image in the second format;
      storing the requested medical image in the second format in the one or more databases;
      storing the generated header associated with the requested medical image in the second format in the file store; and
      passing the requested medical image in the second format to the second format compliant device for viewing.

14. The system of claim 13, wherein the first format is platform dependent.

15. The system of claim 14, wherein the platform dependent first format is the Digital Imaging and Communications in Medicine (DICOM) format.

16. The system of claim 13, wherein the second format is platform independent.

17. The system of claim 16, wherein the platform independent second format is Extensible Markup Language (XML) format.

18. The system of claim 13, further comprising software stored in the device for execution by the one or more processors for:
  identifying a plurality of known image settings corresponding a plurality of devices that display medical images;
  transforming each of the plurality of digital medical images from the first format to a plurality of transformed medical images having formats corresponding to the plurality of known image settings;
  generating a header for each transformed medical image;
  storing each transformed medical image in the one or more databases of the image optimization module; and
  storing each generated header in the file store.

19. The system of claim 13, wherein the one or more image display settings of the second format compliant device include a display resolution and the software transforms the requested medical image by down-sampling a resolution of the requested medical image to the display resolution of the second format compliant.

20. The system of claim 19, further comprising software stored in the device for execution by the one or more processors for compressing the requested medical image in the second format before passing it to the second format compliant device.

21. The system of claim 13 further comprising a server communicatively coupled to the the image store and the image optimization device, said server adapted to pass new images received from one or more image acquisition devices to the image store for storage.

* * * * *